US011871921B2

United States Patent
Breslich (10) Patent No.: US 11,871,921 B2
(45) Date of Patent: Jan. 16, 2024

(54) SUTURE PASSER NEEDLE (71) Applicant: Conmed Corporation, Utica, NY (US)

(72) Inventor: Grady Breslich, Bradenton, FL (US)

(73) Assignee: Conmed Corporation, Utica, NY (US)

( * ) Notice: Subject to any disclaimer, the term of this patent is extended or adjusted under 35 U.S.C. 154(b) by 0 days.

(21) Appl. No.: 15/616,110

(22) Filed: Jun. 7, 2017

(65) Prior Publication Data

US 2017/0347997 A1   Dec. 7, 2017

Related U.S. Application Data (60) Provisional application No. 62/346,664, filed on Jun. 7, 2016.

(51) Int. Cl.
A61B 17/04 (2006.01)
A61B 17/06 (2006.01)
(Continued)

(52) U.S. Cl.
CPC ...... A61B 17/0469 (2013.01); A61B 17/0482 (2013.01); A61B 17/0483 (2013.01);
(Continued)

(58) Field of Classification Search
CPC ............ A61B 17/0469; A61B 17/0482; A61B 17/0483; A61B 17/06; A61B 17/06004; A61B 17/06066; A61B 17/062; A61B 17/0625; A61B 2017/047; A61B 2017/0472; A61B 2017/0475; A61B 2017/0477; A61B 2017/06014; A61B 2017/06019; A61B 2017/06023; A61B 2017/06042; A61B 2017/06076; A61B 2017/0608; A61B 2017/0609; A61B 2017/06095; A61B 2017/00349; A61B 17/04; A61B 2017/06028; A61B 2017/06033; A61B 2017/06038; A61B 2017/06047; A61B 2017/06052;
(Continued)

(56) References Cited

U.S. PATENT DOCUMENTS 5,002,564 A * 3/1991 McGregor ....... A61B 17/06066
112/69
5,312,422 A * 5/1994 Trott ................. A61B 17/0469
604/272

(Continued)

Primary Examiner — Katherine H Schwiker
(74) Attorney, Agent, or Firm — Bond, Schoeneck & King, PLLC; Frederick J. M. Price (57) ABSTRACT This invention relates to surgical suturing devices and methods by which suture may be passed through tissue during surgery, and, more particularly, to an improved blade of a suture passer needle. The suture passer needle includes a first side, a second side, and a blade disposed at an end of the needle. The blade has a first edge extending from the first side of the needle and a second edge extending from the second side of the needle, which converge to a tip of the blade. A notch is disposed in the blade and forms an opening in the first side of the blade. The blade also has one or more cutout portions distal and/or proximal the notch, which minimize the stress and strain placed on the blade. The suture passer needle can be incorporated into surgical suturing devices or suture passer devices to pass suture through a tissue body.

11 Claims, 7 Drawing Sheets (51) Int. Cl.
*A61B 17/062* (2006.01)
*A61B 17/00* (2006.01)
(52) U.S. Cl.
CPC ...... *A61B 17/062* (2013.01); *A61B 17/06066* (2013.01); *A61B 2017/00336* (2013.01); *A61B 2017/00349* (2013.01); *A61B 2017/06042* (2013.01); *A61B 2017/06095* (2013.01)
(58) Field of Classification Search
CPC .... A61B 2017/06085; A61B 2017/061; A61B 2017/06071–06104; A61B 2017/06009–06057
See application file for complete search history.

(56) References Cited

U.S. PATENT DOCUMENTS

| | | | | |
|---|---|---|---|---|
| 5,391,174 A | * | 2/1995 | Weston | A61B 17/0469 606/148 |
| 5,887,594 A | * | 3/1999 | LoCicero, III | A61B 17/064 128/898 |
| 6,723,107 B1 | * | 4/2004 | Skiba | A61B 17/0469 606/144 |
| 7,381,212 B2 | | 6/2008 | Topper et al. | |
| 2003/0065337 A1 | * | 4/2003 | Topper | A61B 17/0625 606/144 |
| 2004/0176802 A1 | * | 9/2004 | Skiba | A61B 17/06109 606/222 |
| 2005/0216048 A1 | * | 9/2005 | Suval | A61B 17/00008 606/194 |
| 2005/0288690 A1 | * | 12/2005 | Bourque | A61B 17/0469 606/144 |
| 2006/0020162 A1 | * | 1/2006 | Whayne | A61B 17/0401 600/37 |
| 2007/0270885 A1 | * | 11/2007 | Weinert | A61B 17/0625 606/139 |
| 2011/0118760 A1 | * | 5/2011 | Gregoire | A61B 17/0483 606/145 |
| 2011/0251626 A1 | * | 10/2011 | Wyman | A61B 17/0469 606/144 |
| 2013/0237997 A1 | * | 9/2013 | Arai | A61B 17/0401 606/144 |
| 2017/0020512 A1 | * | 1/2017 | Murillo | A61B 17/0625 |

* cited by examiner

SUTURE PASSER NEEDLE

CROSS-REFERENCE TO RELATED APPLICATIONS

The present application claims priority to and the benefit of U.S. Provisional Patent Application No. 62/346,664, filed on Jun. 7, 2016, the entire contents of which are hereby incorporated by reference.

FIELD OF THE INVENTION

This invention relates to surgical suturing devices and methods by which suture may be passed through tissue during surgery, and, more particularly, to an improved blade of a suture passer needle.

BACKGROUND

Suturing is a simple procedure when it is performed on external tissues because the needle and suture can be easily manipulated. However, in endoscopic or other minimally invasive surgical procedures that require suturing of internal tissues, access to the suturing area is limited and this limits the ability to manipulate the needle and suture. Instruments and methods for suturing remotely are especially important in these minimally invasive surgical procedures such as laparoscopic and endoscopic procedures.

Minimizing the steps and instrument manipulation required to pass a suture through an internal tissue body and reliably retrieve the suture for subsequent manipulation may result in more streamlined and reliable surgical procedures, shorter surgery duration, and improved patient outcomes. In addition, reduction of the number of access cannulas or instrument ports necessary to perform a procedure will result in decreased tissue trauma. Accordingly there is a need to minimize the number of steps, the repositioning of instruments, and the number of access points during endoscopic suturing procedures.

Systems exist that address this need. For example, U.S. Pat. No. 8,177,796 is directed to surgical suturing devices and methods by which suture may be passed through tissue during surgery. The surgical suturing devices include, in part, a suture passer 100 with a needle 250. See, e.g., FIGS. 1, 3A-3C, 10A-10B and 11D. As shown, the needle 250 includes, in part, a blade 256, notch 260, a side cutout proximal to the notch, and an offset point 258.

Figure 1A:
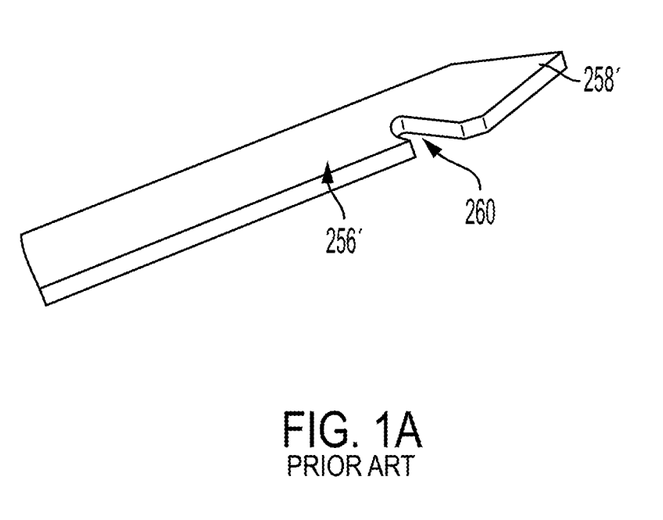
FIG. 1A is a schematic representation of an alternative conventional blade of an alternative surgical suturing device.

Turning to FIG. 1A, a schematic representation of an alternative conventional blade 256' is shown. Blade 256' is part of and works in conjunction with an alternative conventional surgical suturing device, as should be understood by a person of skill in the art in conjunction with a review of this disclosure (although, the alternative conventional surgical suturing device is similar in several respects to suture passer device 100 of U.S. Pat. No. 8,177,796 including the general movement of the blade in the device, i.e., movement in the distal direction followed by movement in a direction at an angle to the distal direction to an extended position as discussed briefly below). Blade 256' has a centered point 258', as opposed to an offset point 258 of blade 256, and does not have a side cutout. The centered point is intended to allow the needle to move in a straight line thought tissue.

However, when either blade 256, 256' is moved to an extended position through a window/jaw of its respective surgical suturing device, it is subject to a relatively large compression load on the notch 260 upon making an approximately 90 degree turn from moving in the distal direction (as shown, for example, in FIGS. 10A, 10B and 11D). This compression load on the needle can weaken, break or crack the blade 256, 256'.

Figure 1B:
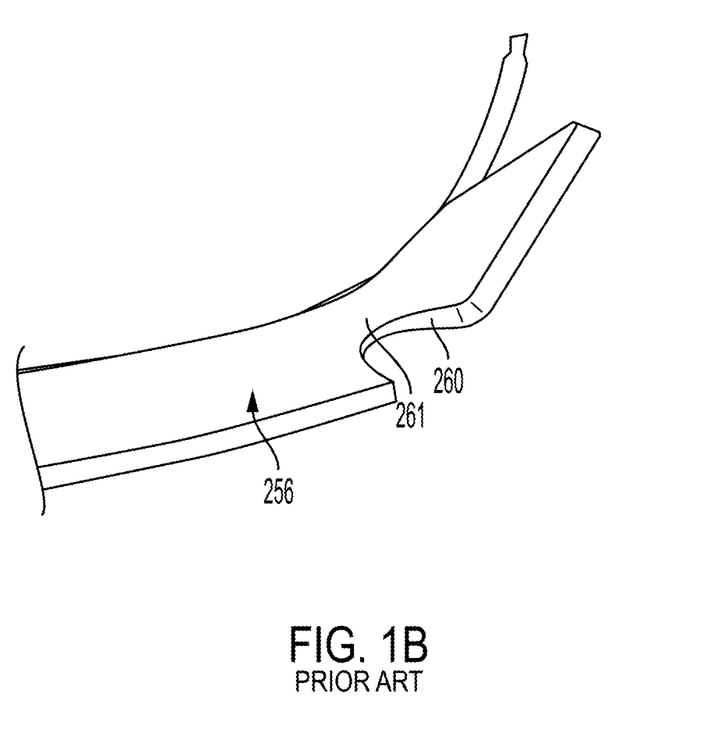
FIG. 1B is a schematic representation of the alternative conventional blade in a partially deployed position through a jaw/window of the alternative surgical suturing device.

Turning to FIG. 1B of the instant disclosure, a schematic representation of the alternative conventional blade 256' of the alternative conventional surgical suturing device is shown in a partially deployed position through the device's jaw/window (the window is not shown in this Figure in order to show an unobstructed blade 256'). Areas of high strain 261 are shown on blade 256' near the notch 260. The region distal of the notch 261 is in a portion of the jaw/window where the curvature, and thus pressure and strain on the blade 256', is high. However, the blade 256' remains straight relative to the material near the notch. Accordingly there is a need to minimize the stress/strain placed on the blade 256 and to decrease the breakage/crack formation when it is moved to an extended position through the window.

Description of the Related Art Section Disclaimer: To the extent that specific patents/publications/products are discussed above in this Background Section or elsewhere in this Application, these discussions should not be taken as an admission that the discussed patents/publications/products are prior art for patent law purposes. For example, some or all of the discussed patents/publications/products may not be sufficiently early in time, may not reflect subject matter developed early enough in time and/or may not be sufficiently enabling so as to amount to prior art for patent law purposes. To the extent that specific patents/publications/products are discussed above in this Background Section and/or throughout the application, the descriptions/disclosures of which are all hereby incorporated by reference into this document in their respective entirety(ies).

SUMMARY OF THE INVENTION

The present disclosure is directed to inventive devices and methods for passing suture through tissue during surgery. Various embodiments and implementations herein are directed to an improved blade of a needle of a surgical suturing device. The blade can be designed to be more flexible, bend more evenly, have reduced stress/lowered compression load on the distal tip near the notch as compared to conventional surgical suturing device blades upon deployment through a jaw/window at a distal end of the device. This functionality can be accomplished by removing material from the blade proximately and/or distally of the notch in the blade, as further discussed in the Detailed Description of the Embodiments section below in conjunction with the referenced Figures. Further, the blade can include non-linear edge portions leading to a distal point or tip. The non-linear edge portions can include a radius of curvature that can be the same or can be different from each other.

In one embodiment, the suture passer needle can include a first side, a second side, and a blade disposed at a first (e.g., distal) end of the needle. The blade has a first edge extending from the first side of the needle and a second edge extending from the second side of the needle, each of which converge to a tip of the blade (which can be centered or offset). A notch is disposed in the blade and forms an opening in the first side of the blade. The blade can also have one or more cutout portions distal and/or proximal to the notch, which are configured to minimize the stress and strain placed on the blade while in use. The cutout portions are preferably completely surrounded by a portion of the body of the blade.

In an alternative embodiment, the notch of the previously described suture passer needle can have a distal end and a proximal end. The distal end of the notch converges to a point with the first edge of the blade. Further, the first edge and the second edge of the blade are both nonlinear, can be curved, and can preferably have an equal radius of curvature (but do not need to have an equal radius of curvature, i.e., one edge can have a radius of curvature larger than the other).

In another embodiment, the suture passer needle can be incorporated into a surgical suturing device (or suture passer device). The system can include a jaw member disposed at a distal end of a suturing apparatus, which has an aperture extending therethrough. The suture passer needle can be extended through the aperture of the suturing apparatus to carry a portion of suture through the aperture. The system can also include a capture feature formed on the distal end of the suturing system, which is actuatable to releasably grip and retain suture. The suturing system can be actuatable by a single actuation of an actuation mechanism to move the needle through a tissue body and the aperture, and to actuate the capture feature to firmly and releasably grip the portion of suture after the portion of suture has been carried by the needle through the tissue body and the aperture.

BRIEF DESCRIPTION OF THE DRAWINGS

The present invention will be more fully understood and appreciated by reading the following Detailed Description in conjunction with the accompanying drawings. The accompanying drawings illustrate only typical embodiments of the disclosed subject matter and are therefore not to be considered limiting of its scope, for the disclosed subject matter may admit to other equally effective embodiments.

Reference is now made briefly to the accompanying drawings, in which.

Where applicable, like reference characters designate identical or corresponding components and units throughout the several views, which are not to scale unless otherwise indicated. Moreover, the embodiments disclosed herein may include elements that appear in one or more of the several views or in combinations of the several views.

DETAILED DESCRIPTION OF EMBODIMENTS

Figure 1C:
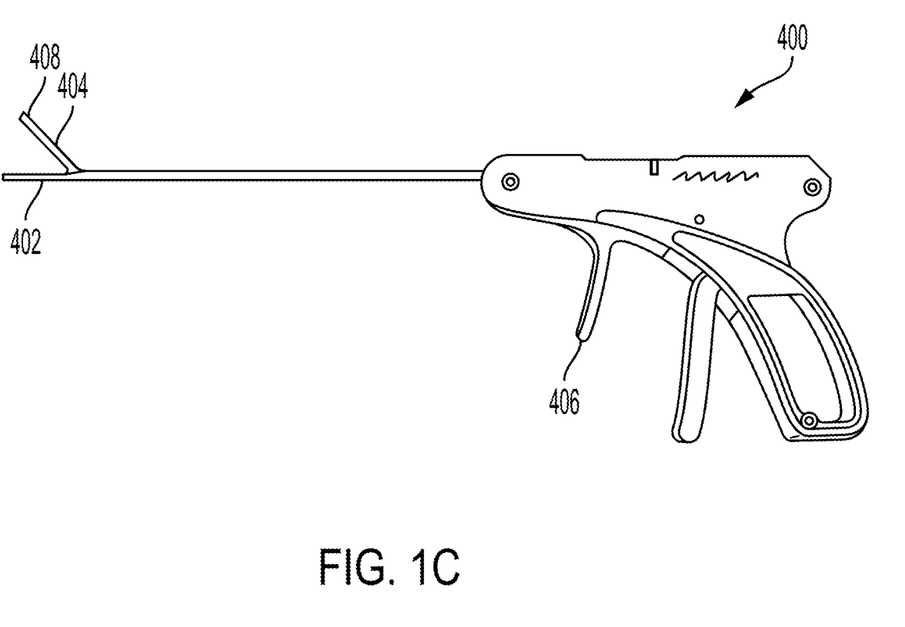
FIG. 1C is a schematic representation of the SPECTRUM® AUTOPASS™ suture passer.
Figure 2A:
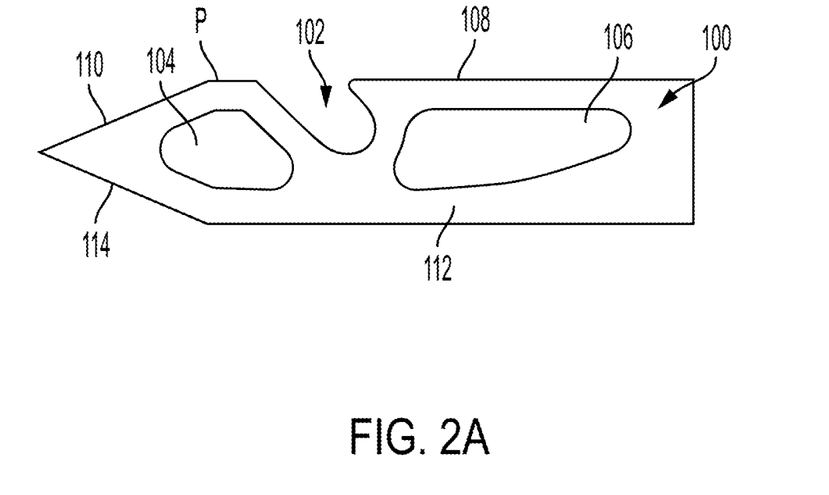
FIG. 2A is a schematic side view representation of an improved blade of a surgical suturing device according to an embodiment.
Figure 2B:
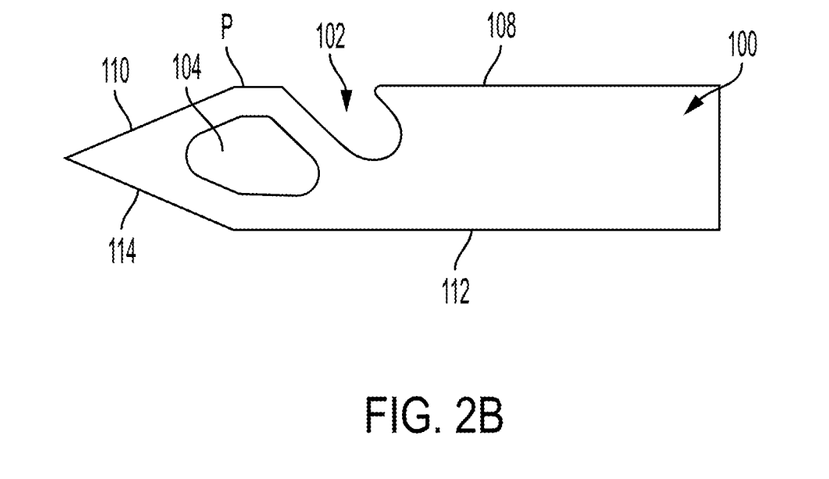
FIG. 2B is a schematic side view representation of an improved blade of a surgical suturing device according to an embodiment.
Figure 3A:
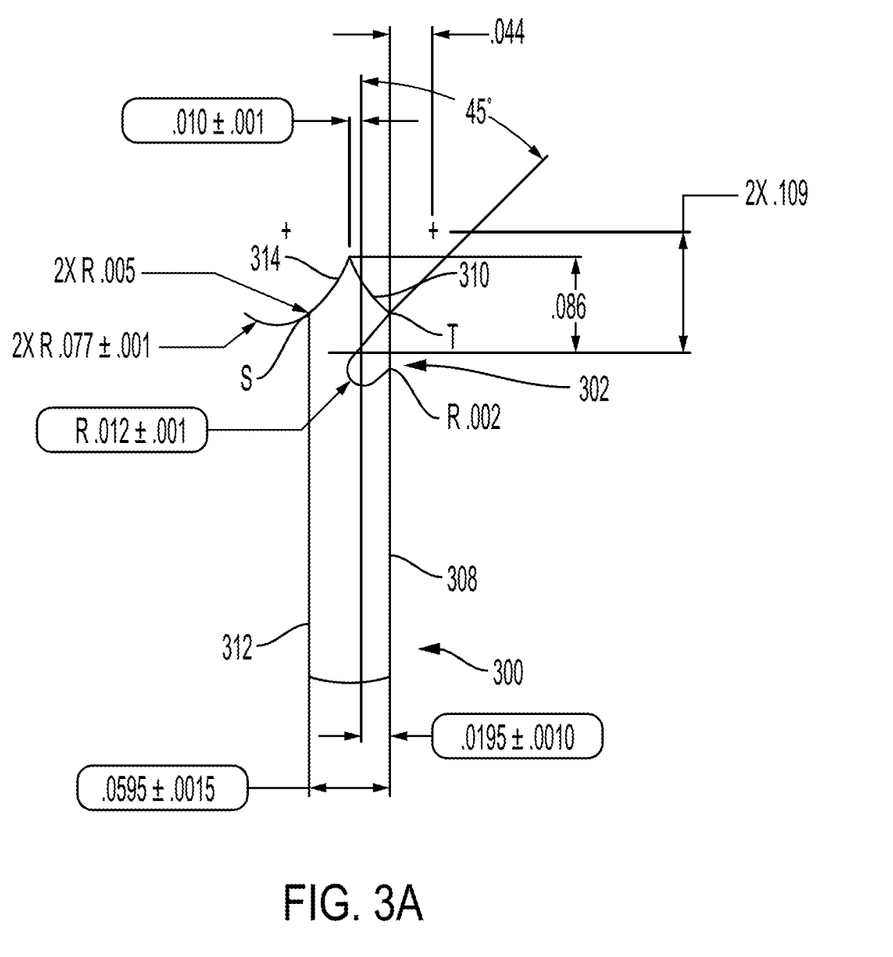
FIG. 3A is a schematic side view representation of an improved blade of a surgical suturing device according to an alternative embodiment.
Figure 3B:
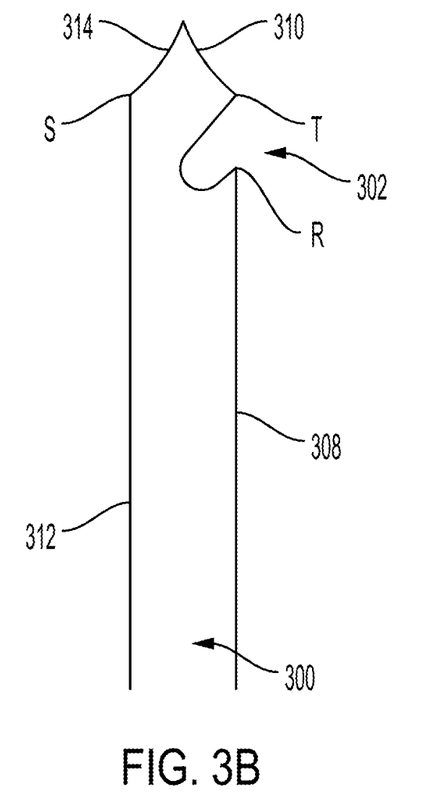
FIG. 3B is a magnified schematic representation of the embodiment shown in FIG. 3A.

Embodiments of the improved blade 100 of a needle, described with respect to FIGS. 2A and 2B herein, and an improved blade 300 of a needle, described with respect to FIGS. 3A and 3B, are designed to be a part of and be used in conjunction with surgical suturing devices (or suture passer devices) such as the SPECTRUM® AUTOPASS™ suture passer (as should be understood and appreciated by a person of ordinary skill in the art in conjunction with a review of this disclosure), the structure and design of which is incorporated by reference herein in its entirety. For example, the SPECTRUM® AUTOPASS™ suture passer 400 shown in FIG. 1C includes, generally, a jaw member 402 at a distal end of the suture passer 400, a needle 408 which can be retracted and extended through the jaw member 402 relative to the distal end of the suture passer 400, and a capture feature 404 on the distal end of the suture passer 400, which is actuatable to releasably grip and retain suture. Upon a single actuation of an actuation mechanism 406, the needle 408 moves from a retracted position to an extended position through the aperture of the jaw member 402 and the tissue body. Certain aspects such as the proximal and distal "cutout" portions can also be incorporated into blade 256 as described and shown in U.S. Pat. No. 8,177,796 (as should be understood and appreciated by a person of ordinary skill in the art in conjunction with review of this disclosure), which is incorporated by reference herein in its entirety. The descriptions of the positioning and use of needle 250 and blade 256 in U.S. Pat. No. 8,177,796 can generally apply to the embodiments of the improved blade portions of a needle described herein, and only the improved structure of the embodiments of the improved blade and resultant functionality will be additionally described herein.

Referring to FIG. 2A, in one embodiment, a schematic side view representation of an improved blade 100 of needle 250 (shown and described in U.S. Pat. No. 8,177,796) is shown. The blade 100 can include, but is not limited to, a notch 102, and a plurality of "cutout" portions—distal cutout portion 104 and proximal cutout portion 106 ("distal" and "proximal" with respect to the notch 102). The cutout portions (104, 106) can be formed by first forming the blade 100 and then removing material from the blade 100, or the blade 100 with the cutout portions (104, 106) can be formed in the first instance per a molding procedure (as should be understood by a person of skill in the art in conjunction with a review of this disclosure). The actual geometry and size of the region or regions of removed material may vary, and it can be optimized based on application and the geometry of the device it interacts with (as should be understood by a person of skill in the art in conjunction with a review of this disclosure). Blade 100 is also shown with a centered point 258', as opposed to an offset point 258 of blade 256, and does not have a side cutout (although, Blade 100 can include an offset point). Blade 100 (and blade 300, described below) can be made from any material with sufficient ability to bend at an angle within the suture passer (as described herein), and with enough stiffness to pierce and be pushed through tissue (as should be appreciated by a person of skill in the art in conjunction with a review of this disclosure) including steel, plastics, or other shape memory or super-elastic materials. In a particular example, blade 100 (and blade 300) can be made from nitinol (a nickel-titanium alloy with shape memory and super-elastic properties).

Referring to FIG. 2B, in another embodiment, a schematic side view representation of an improved blade 100 of needle 250 is shown. The blade 100 shown in FIG. 2B includes only a distal cutout portion 104. Alternatively, blade 100 could have only a proximal cutout portion 106, or a plurality of proximal cutout portions 106 and/or a plurality of distal cutout portions 104.

Providing the cutout portions (104, 106) on the interior of the blade 100 without disrupting the outer surface, as opposed to the blade shown in U.S. Pat. No. 8,177,796, has the particular advantage of not changing the primary contact surfaces that interact with the surgical suturing device. Removing material from the outer edges can cause the needle to deflect side-to-side in the surgical suturing device, to catch on surfaces of the device and get stuck/jammed, or to be deflected by tissue when it is used with the device.

In both FIGS. 2A and 2B, the notch 102 is formed through a first side 108 of the blade 100. The tip of the blade 100 has a first edge 110 that converges with the first side 108 at a point (P). Similarly, the tip of the blade 100 has a second edge 114 that converges with a second side 112 of the blade 100. As depicted in the embodiment shown in FIGS. 2A-2B, the first side 108 of the blade 100 converges with the first edge 110 of the tip of blade 100 at a point (P) distal with respect to the notch 102.

Referring now to FIGS. 3A-3B, there are shown schematic representations of an alternate embodiment of a blade 300 of needle 250. Similar to the embodiments shown in FIGS. 2A-2B, the blade 300 comprises a first side 308, which is opposite a second side 312 of the blade 300 and comprises a notch 302 having an opening for receiving suture material. A first edge 310 extends from the tip of the blade 300 to a distal end (T) of the first side 308 of the blade 300. Similarly, a second edge 314 extends from the tip of the blade 300 to a distal end (S) of the second side 312 of the blade 300. In the embodiment shown in FIG. 3A, the first edge 310 can be non-linear and include a radius of the curvature that can be equivalent to a radius of the curvature of the second edge 314.

As previously discussed, the distal ends (S, T) are located opposite each other on their respective sides of the blade 300. The notch 302 on the first side 308 of the blade 300 is positioned proximal to the distal end (T) of the first side 308 of the blade 300 and extends to the distal end (T) of the first side 308 of the blade 300. The notch 302 also extends to a proximal end (R) positioned on the first side 308 of the blade 300 proximal to the opening of the notch 302. When viewed along an axis extending from a proximal end to a distal end of the blade 300 in a direction toward the needle tip, proximal end (R) and distal end (T) are aligned in that direction along the first side 308 of the blade 300. Stated differently, distal end (T) and proximal end (R) extend the same distance in a perpendicular direction from a central longitudinal axis extending along the length of the blade 300. Cutout portions (104, 106) as shown in FIGS. 2A-2B can be incorporated into the blade 300 shown in FIGS. 3A-3B (as should be understood and appreciated by a person of ordinary skill of the art in conjunction with a review of this disclosure).

While embodiments of the present invention have been particularly shown and described with reference to certain exemplary embodiments, it will be understood by one skilled in the art that various changes in detail may be effected therein without departing from the spirit and scope of the invention as defined by claims that can be supported by the written description and drawings. Further, where exemplary embodiments are described with reference to a certain number of elements it will be understood that the exemplary embodiments can be practiced utilizing either less than or more than the certain number of elements.

The invention claimed is:

1. A suture passer needle, comprising:
an elongated planar body having a first side, a second side, a first distal end and a second proximal end, and a blade disposed at the first distal end of the body;
the blade having a first edge extending from a single pointed edge where the first side and the blade meet, and a second edge extending from the second side, which converge to a tip of the blade, wherein the single pointed edge and the first side are equidistant from the central axis;
a first cutout portion positioned in the blade, wherein the first cutout portion is surrounded by a first portion of the body and is positioned proximally to a notch; a second cutout portion in the blade positioned distally to the notch;
the notch being disposed in the first side of the body, forming an opening in the first side of the body, wherein the notch comprises a first proximal notch side and a second distal notch side, wherein the first proximal notch side and the second distal notch side are connected by a u-shaped end, wherein each of the first proximal notch side and the second distal notch side face the opening, extend from the first side of the body toward the second proximal end of the body and extend at an angle to a central axis extending along the body; and
a distal end of the notch, which converges with the first edge to form the single pointed edge, and wherein the second side consists of a surface extending in a single plane.

2. The needle of claim 1, further comprising a proximal end of the notch aligned along the first side of the body with the distal end of the notch.

3. The needle of claim 2, wherein the proximal end of the notch and the distal end of the notch are equidistant from the central axis.

4. The needle of claim 1, wherein the first edge is concaved shaped and the second edge is concaved shaped, wherein a radius of curvature of the concaved shaped first edge is equal to a radius of the curvature of the concaved shaped second edge.

5. A suturing system for passing suture through a tissue body, comprising:
a first jaw member disposed at a distal end of the suturing system, the first jaw member having an aperture extending therethrough;
a needle having an elongated planar body having a first side, a second side, a first distal end and a second proximal end, and a blade disposed at the first distal end of the body, the blade having a first edge extending from a single pointed edge where the first side and the blade meet, and a second edge extending from the second side, which converge to a tip of the blade, wherein the single pointed edge and the first side are equidistant from the central axis, a first cutout portion positioned in the blade being surrounded by a first portion of the body and is positioned proximally to the notch, a second cutout portion in the blade positioned distally to the notch, the notch being disposed in the first side of the body, forming an opening in the first side of the body, wherein the notch comprises a first proximal notch side and a second distal notch side, wherein the first proximal notch side and the second distal notch side are connected by a u-shaped end, wherein each of the first proximal notch side and the second distal notch side face the opening, extend from the first side of the body toward the second proximal end of the body and extend at an angle to a central axis extending along the body, and wherein the second side consists of a surface extending in a single plane, the needle being configured to extend through the aperture and configured to carry a portion of suture through the aperture, and wherein a distal end of the notch, which converges with the first edge to form the single pointed edge;

a capture feature formed on the distal end of the suturing system;

wherein the suturing system is actuatable by a single actuation of an actuation mechanism to move the needle through the tissue body and the aperture, and to cause the capture feature to firmly and releasably grip the portion of suture after the portion of suture has been carried by the needle through the tissue body and the aperture.

6. The system of claim 5, wherein the first edge and the second edge are linear and equal in length.

7. The system of claim 5, wherein a proximal end of the notch and a distal end of the notch are equidistant from the central axis.

8. The system of claim 5, wherein the first edge and the second edge are curved.

9. The system of claim 5, wherein the first edge is concaved shaped and the second edge is concaved shaped, wherein a radius of curvature of the concaved shaped first edge is equal to a radius of curvature of the concaved shaped second edge.

10. The needle of claim 5, further comprising a proximal end of the notch aligned along the first side of the body with a distal end of the notch.

11. The needle of claim 5, wherein the first edge is concaved shaped and the second edge is concaved shaped.

* * * * *